United States Patent [19]
Ukigaya et al.

[11] Patent Number: 5,589,191
[45] Date of Patent: Dec. 31, 1996

[54] SLOW-RELEASE SODIUM VALPROATE TABLETS

[75] Inventors: Tadashi Ukigaya; Hirotaka Endoh, both of Saitama, Japan

[73] Assignee: Nikken Chemicals Co., Ltd., Tokyo, Japan

[21] Appl. No.: 485,138

[22] Filed: Jun. 7, 1995

Related U.S. Application Data

[63] Continuation of Ser. No. 67,107, May 26, 1993, abandoned.

[30] Foreign Application Priority Data

May 29, 1992 [JP] Japan .................................. 4-161785

[51] Int. Cl.$^6$ ...................................... A61K 9/36
[52] U.S. Cl. .................... 424/480; 424/495; 424/489; 424/471
[58] Field of Search ..................... 424/495, 480, 424/489, 471

[56] References Cited

U.S. PATENT DOCUMENTS

| | | | |
|---|---|---|---|
| 4,684,516 | 8/1987 | Bhutani | 424/471 |
| 5,017,613 | 5/1991 | Aubert et al. | 514/557 |
| 5,019,398 | 5/1991 | Daste | 424/480 |
| 5,055,306 | 10/1991 | Barry et al. | 424/480 |
| 5,185,159 | 2/1993 | Aubert et al. | 424/489 |

FOREIGN PATENT DOCUMENTS

| | | |
|---|---|---|
| 0315414 | 11/1988 | European Pat. Off. ......... A61K 9/54 |
| 0342522 | 11/1989 | European Pat. Off. . |
| 62-084020 | 4/1987 | Japan . |
| 62-81309 | 4/1987 | Japan . |

*Primary Examiner*—Thurman K. Page
*Assistant Examiner*—William E. Benston, Jr.
*Attorney, Agent, or Firm*—Sughrue, Mion, Zinn, Macpeak & Seas

[57] ABSTRACT

A slow, release sodium valproate tablet with a coating layer, obtained by coating a core containing sodium valproate with a coating agent comprising ethyl cellulose having silicic acid anhydride dispersed therein. The slow-release tablets, while having a relatively small size, maintain a stable dissolution rate without being influenced by pH conditions to stably maintain the blood concentration of active agent over an extended period of time.

5 Claims, 5 Drawing Sheets

SLOW-RELEASE SODIUM VALPROATE TABLETS

This is a Continuation of application Ser. No. 08/067,107 filed 26 May 1993 abandoned.

FIELD OF THE INVENTION

This invention relates to slow-release sodium valproate tablets.

BACKGROUND OF THE INVENTION

Sodium valproate (2-propylpentanoic acid sodium salt) is a useful drug widely employed for treatment of epilepsy and prevention of ictus epilepticus. The effective blood concentration of the drug generally ranges from 50 to 100 µg/ml. Because sodium valproate has a short biological half-life, sodium valproate must be administered three times a day to maintain an effective blood concentration. Since such a short dose interval is troublesome for patients, there have been many efforts to develop long-acting, slow-release preparations of sodium valproate.

However, sodium valproate should be administered at a relatively high daily dose approaching 1200 mg. Moreover, sodium valproate is highly hygroscopic. Hence, conventional slow-release tablets comprise a relatively large proportion of adjuvants, such as retarders, and therefore are unsatisfactorily weighty and bulky.

Recently proposed techniques for preparing slow-release tablets of sodium valproate include (a) a process comprising preparing granules from a mixture of sodium valproate and magnesium aluminometasilicate using ethyl cellulose as a binder and tableting the same (see JP-A-62-81309, the term "JP-A" as used herein means an "unexamined published Japanese patent application") and (b) a process comprising mixing valproic acid, having ethyl cellulose dissolved therein, with a mixture of Eudragit (an acrylic polymer) manufactured by Rohm Pharma and sodium valproate, followed by granulation and tableting of the same (see U.S. Pat. No. 5,017,613 corresponding to JP-A-60-41610).

The slow-release tablets obtained by process (a) do not maintain the optimal blood concentration, with the concentration decreasing considerably after 10 hours of administration. The slow-release tablets obtained by process (b) are pH sensitive. Hence, the rate of drug dissolution varies with the pH in the various portions of the digestive tract and thus the blood concentration is susceptible to wide variation.

SUMMARY OF THE INVENTION

An object of the instant invention is to provide slow-release sodium valproate tablets which are relatively compact, easy to ingest and can be administered once a day.

Another object of the instant invention is to provide slow-release sodium valproate tablets which dissolves at a stable rate irrespective of pH conditions.

As a result of extensive investigation, the instant inventors have found that sodium valproate preparations obtained by coating sodium valproate cores with ethyl cellulose, having uniformly dispersed therein silicic acid anhydride, while having a relatively small size, have a constant rate of dissolution under varying pH conditions and exhibit stable and satisfactory slow release properties. The instant invention has been completed based on that finding.

The instant invention relates to a slow-release sodium valproate tablet with a coating layer, obtained by coating a core containing sodium valproate with a coating agent comprising ethyl cellulose having dispersed therein silicic acid anhydride.

DETAILED DESCRIPTION OF THE INVENTION

Figure 1:
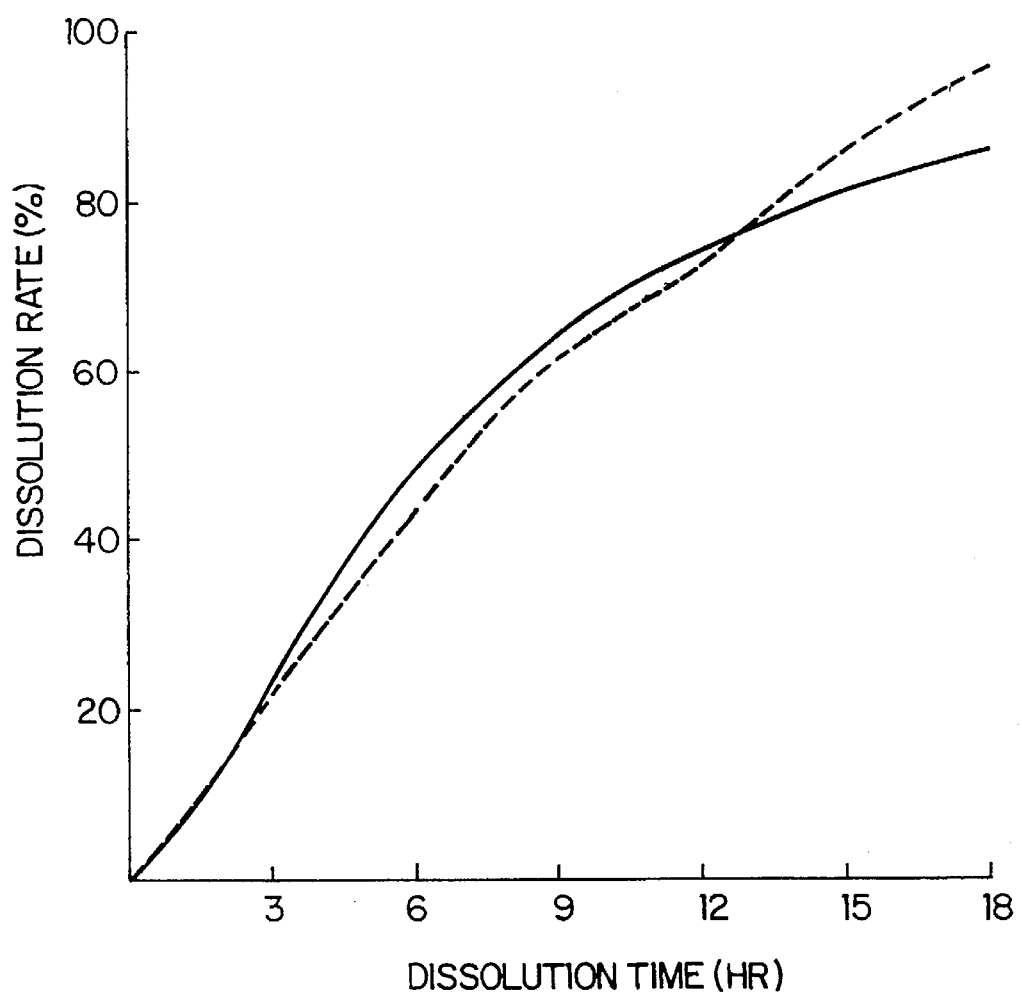
FIG. 1 is a graph of dissolution rate of sodium valproate over time of slow-release tablets of the present invention (Tablet A). A solid line and a dotted line stand for distilled water and J. P. first solution, respectively.
Figure 2:
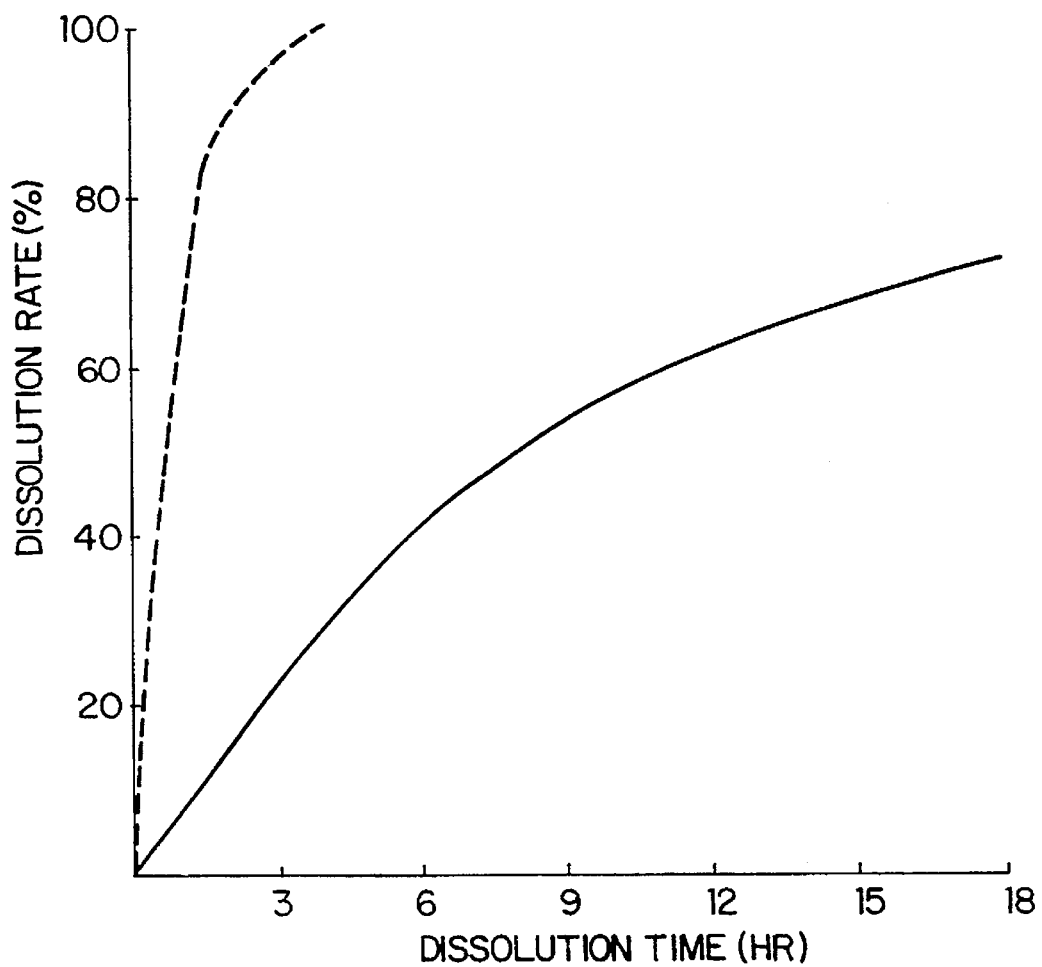
FIGS. 2 to 4 each is a graph of dissolution rate of sodium valproate over time of comparative tablets (Tablets B, C and D). A solid line and a dotted line stand for distilled water and J. P. first solution, respectively.
Figure 3:
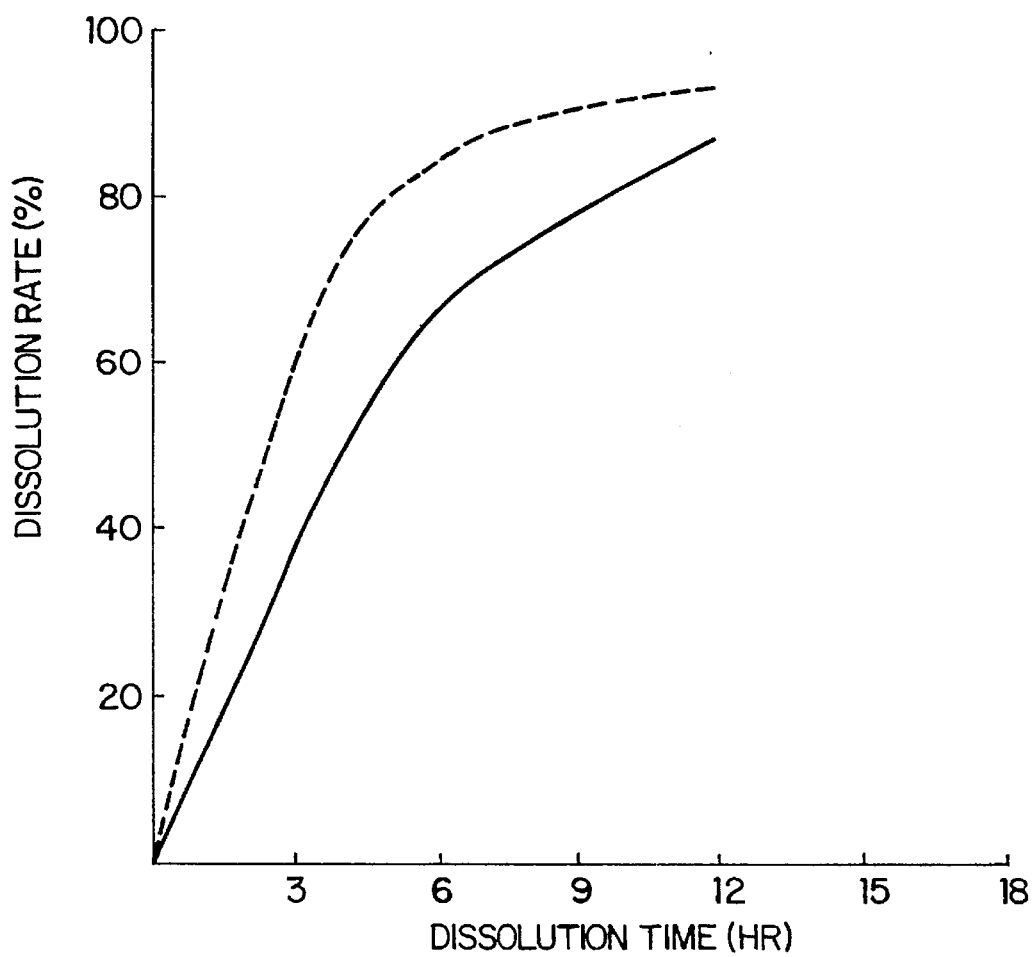
Figure 4:
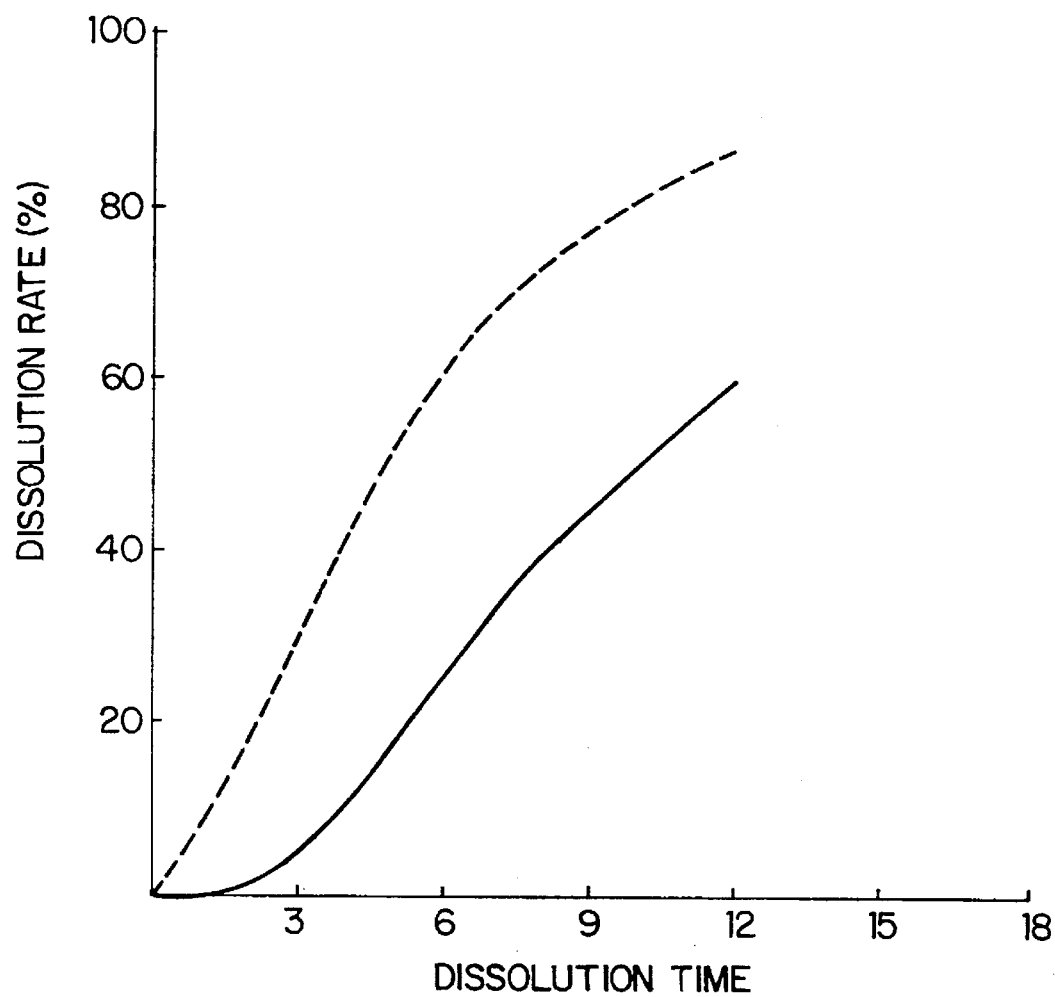

Cores of the sodium valproate tablets which can be used in the instant invention are not limited particularly, and any sodium valproate tablets prepared by conventional techniques can be used as they are. Such tablets are prepared by, for example, uniformly mixing sodium valproate with adjuvants, such as vehicles and binders, granulating the mixture in a usual manner, adding appropriate lubricants thereto, followed by punching.

Adjuvants, which are used for improvement of molding properties, regulation of granule size and protection against moisture, include vehicles, such as silicic acid anhydride, higher fatty acid metal salts (e.g., calcium or magnesium salt of stearic acid, palmitic acid or myristic acid); binders, such as hydroxypropyl cellulose, polyethylene glycol and polyvinylpyrrolidone; and lubricants, such as calcium stearate, magnesium stearate, white carbon and silicic acid anhydride.

The slow-release sodium valproate tablets of the instant invention are prepared by coating cores containing sodium valproate with an ethyl cellulose solution, having silicic acid anhydride uniformly dispersed therein, by spray coating in a usual manner.

Silicic acid anhydride which can be used in the coating agent is selected from those species which are insoluble in water and dispersible in water or organic solvents to form colloidal suspensions.

Coating agents are prepared by dissolving ethyl cellulose in a lower alcohol, e.g., methyl alcohol or ethyl alcohol, at a concentration of from about 2 to 10% by weight, preferably from 4 to 6% by weight, and dispersing therein from 0.1 to 0.7 parts by weight, and preferably from 0.2 to 0.5 parts by weight, per part by weight of ethyl cellulose, of silicic acid anhydride. The coating agent usually is applied to the core in an amount of from about 2 to 10% by weight, and preferably from about 3 to 8% by weight, based on the weight of the core.

The rate of dissolution of sodium valproate from the slow-release tablets thus obtained may be controlled by varying the mixing ratio of silicic acid anhydride in the coating agent or the amount of the coating agent applied. The higher the silicic acid anhydride ratio or the lower the amount of the coating agent, the faster the overall dissolution of the tablets. Conversely, the lower the silicic acid anhydride ratio or the higher the amount of the coating agent, the slower the overall dissolution of the tablets, meaning slower release of the active agent.

Further, at a higher silicic acid anhydride mixing ratio, the dissolution rate is less dependent on the amount of coating agent and it is possible to obtain stable tablets. However, at too high a silicic acid anhydride mixing ratio, the tablets may not exhibit slow release properties. For those reasons, the silicic acid anhydride mixing ratio preferably is selected from the above range.

The technique of the instant invention also can be applied to preparations of other similar drugs having high water solubility.

The instant invention now will be illustrated in greater detail by way of Examples, Comparative Examples and Test Examples, but it should be understood that the instant invention is not to be construed as being limited thereby. All the percents are given by weight unless otherwise indicated.

EXAMPLE 1

(a) Preparation of Cores:

Sodium valproate weighing 1600 g and 160 g of silicic acid anhydride, "Aerosil-200" (a product of Nippon Aerosil Co., Ltd.), were mixed thoroughly, and the mixture was kneaded with 608 g of an ethanol solution containing 5% hydroxypropyl cellulose. The blend was dried in a hot air drier at 60° C. and passed through a 16-mesh sieve. The resulting granules were mixed with 1% calcium stearate and compression molded to obtain core tablets each weighing 228.6 mg and having a diameter of 8.5 mm.

(b) Preparation of Slow-release Tablets:

A thousand core tablets obtained in (a) above were fluidized in a fluidized bed coating apparatus, "Uniglat" (manufactured by Okawara Seisakusho Co.) and spray-coated with a coating agent comprising a 5% ethanol solution of ethyl cellulose (ethoxy content: 46 to 51%) having dispersed therein 1% Aerosil-200 to obtain slow-release sodium valproate tablets each weighing 236.3 mg (the coating layer weight: 7.7 mg). The resulting coated tablets were designated tablets A.

EXAMPLE 2

Slow-release sodium valproate tablets (designated tablets E, F or G) Were prepared in the same manner as in Example 1, except that 1000 core tablets each weighing 226.7 mg and having a diameter of 8.5 mm were fluidized in a fluidized bed coating apparatus, "Uniglat" (manufactured by Okawara Seisakusho Co.) and spray-coated with a coating agent comprising a 5% ethanol solution of ethyl cellulose (ethoxy content: 46 to 51%) having dispersed therein Aerosil-200 in an amount varying from 1 to 1.5%. The particulars of the resulting coated tablets are shown below.

|  | Tablets E | Tablets F | Tablets G |
| --- | --- | --- | --- |
| Aerosil-200 | 1% | 1.25% | 1.5% |
| Tablet Weight | 234.5 mg | 237.5 mg | 243.3 mg |
| Coating Layer Weight | 7.8 mg | 10.8 mg | 16.6 mg |

EXAMPLE 3

Sodium valproate weighing 400 g and 80 g of Aerosil-200 were mixed thoroughly, and the mixture was kneaded with 216 g of an ethanol solution containing 5% hydroxypropyl cellulose. The blend was dried in a hot air drier at 60° C. and passed through a 16-mesh sieve. The resulting granules were mixed with 1% calcium stearate and compression molded to obtain core tablets each weighing 246.2 mg and having a diameter of 8.5 mm.

A thousand core tablets thus obtained were spray-coated with a coating agent comprising a 5% ethanol solution of ethyl cellulose (ethoxy content: 46 to 51%) having dispersed therein 1.25% Aerosil-200 in the same manner as in Example 2 to obtain slow-release sodium valproate tablets (designated tablets H) each weighing 256.4 mg (the coating layer weight: 10.2 mg).

EXAMPLE 4

Sodium valproate weighing 400 g, 40 g of Aerosil-200 and 10 g of a carboxyvinyl polymer were mixed thoroughly and kneaded with 140 g of a 5% ethanol solution of hydroxypropyl cellulose. The blend was dried in a hot air drier at 60° C. and passed through a 16-mesh sieve. The granules were mixed with 1% magnesium stearate and then punched out to obtain core tablets each weighing 231.2 mg and having a diameter of 8.5 mm.

A thousand core tablets were spray-coated with a coating agent comprising a 5% ethanol solution of ethyl cellulose (ethoxy content: 46 to 51%) having dispersed therein 1% Aerosil-200 in the same manner as in Example 2 to obtain slow-release sodium valproate tablets (designated tablets I) each weighing 239.9 mg (coating layer weight: 8.7 mg).

EXAMPLE 5

Sodium valproate weighing 600 g and 120 g of Aerosil-200 were mixed thoroughly and kneaded with 348 g of a 5% ethanol solution of hydroxypropyl cellulose. The blend was dried in a hot air drier at 60° C. and passed through a 16-mesh sieve. The granules were mixed with 1% magnesium stearate and then compression molded to obtain core tablets each weighing 454.6 mg and having a diameter of 10.5 mm.

A thousand core tablets were spray-coated with a coating agent comprising a 5% ethanol solution of ethyl cellulose (ethoxy content: 46 to 51%) having dispersed therein 1.25% Aerosil-200 in the same manner as in Example 2 to obtain slow-release sodium valproate tablets (designated tablets J) each weighing 472.9 mg (coating layer weight: 18.3 mg).

EXAMPLE 6

Three thousand core tablets each weighing 226.8 mg and having a diameter of 8.5 mm which were prepared in the same manner as in Example 1-(a) were spray-coated with a coating agent comprising a 5% ethanol solution of ethyl cellulose (ethoxy content: 46 to 51%) having dispersed therein 2.5% Aerosil-200 while being rotated by means of an automatic film coating apparatus, "FM 2S" (manufactured by Freund Industrial Co., Ltd.) to obtain slow-release sodium valproate tablets (designated tablets K) each weighing 240.1 mg (coating layer weight: 13.3 mg).

COMPARATIVE EXAMPLES 1 TO 3

A thousand core tablets obtained in Example 1-(a) were spray-coated in the same manner as in Example 1-(b), except for using, as a coating agent, a 5% ethanol solution of ethyl cellulose (ethoxy content: 46 to 51%) (Comparative Example 1), a 5% ethanol solution of ethyl cellulose (ethoxy content: 46 to 51%) having dispersed therein 1% calcium stearate (Comparative Example 2), or a 5% ethanol solution of ethyl cellulose (ethoxy content: 46 to 51%) having dispersed therein 1% fatty acid monoglyceride, "Myvacet" (produced by Eastman Kodak Co.), to prepare tablets B each weighing 233.1 mg (coating layer weight: 4.5 mg), tablets C each weighing 233.0 mg (coating layer weight: 4.4 mg) and tablets D each weighing 234.5 mg (coating layer weight: 5.9 mg), respectively.

TEST EXAMPLE 1

Dissolution Test

Tablets A prepared in Example 1 and tablets B, C and D prepared in Comparative Examples 1 to 3 were tested according to the second method of dissolution test (paddle method) specified in Pharmacopoea Japonica, 12th Ed. (hereinafter referred to J. P.) (number of rotation: 100 rpm) using as a testing solution, 900 ml of water (distilled water) or a first solution (pH=1.2) specified in the J.P. disintegration test.

Samples were obtained at various time points, and the amount of dissoluted sodium valproate was measured by HPLC. The results obtained are shown in Table 1 and in FIGS. 1 to 4.

TABLE 1

| Tablet | Testing Solution | Dissolution Rate of Sodium Valproate (%) Time of Dissolution (hr) | | | | | | | |
|---|---|---|---|---|---|---|---|---|---|
| | | 2 | 4 | 6 | 8 | 10 | 12 | 15 | 18 |
| A | distilled water | 13.7 | 32.8 | 47.9 | 59.2 | 68.2 | 74.0 | 81.1 | 86.1 |
| | J.P. first solution | 14.1 | 29.4 | 43.1 | 56.2 | 65.2 | 72.2 | 86.0 | 95.8 |
| B | distilled water | 14.8 | 29.9 | 41.2 | 49.9 | 56.9 | 61.9 | 68.1 | 72.8 |
| | J.P. first solution | 95.6 | 99.8 | | | | | | |
| C | distilled water | 24.2 | 49.2 | 66.0 | 74.1 | | 86.7 | | |
| | J.P. first solution | 41.0 | 72.3 | 83.7 | 88.8 | | 92.8 | | |
| D | distilled water | 1.5 | 11.2 | 25.3 | 39.1 | | 59.5 | | |
| | J.P. first solution | 18.1 | 42.1 | 60.5 | 73.1 | | 86.9 | | |

The results of the dissolution test reveal that the sodium valproate tablets A according to the instant invention show practically the same dissoluting behavior in both water and the J.P. first solution (pH=1.2) over a long period of time, thereby establishing the pH-independent nature of the slow-release tablets of the instant invention. To the contrary, tablets B using ethyl cellulose only as a coating agent, tablets C using ethyl cellulose in combination with calcium stearate as a coating agent and tablets D using ethyl cellulose in combination with a fatty acid monoglyceride as a coating agent exhibit faster dissolution in the J.P. first solution than in water, indicating that the coating agents used in tablets B, C and D fail to furnish pH-independent slow-release tablets.

TEST EXAMPLE 2

Dissolution Test

A dissolution test was conducted on tablets E to K prepared in Examples 2 to 6 in the same manner as in Test Example 1. The results obtained are shown in Table 2 below.

TABLE 2

| Tablet | Testing Solution | Dissolution Rate of Sodium Valproate (%) Time of Dissolution (hr) | | | | | | | |
|---|---|---|---|---|---|---|---|---|---|
| | | 2 | 4 | 6 | 8 | 10 | 12 | 15 | 18 |
| E | distilled water | 11.6 | 30.4 | 45.1 | 57.0 | | 74.9 | | 88.2 |
| | J.P. first solution | 11.8 | 25.3 | 39.6 | 52.5 | | 80.5 | | 95.7 |
| F | distilled water | 11.8 | 31.2 | 45.9 | 57.7 | | 76.3 | | 89.5 |
| | J.P. first solution | 12.5 | 26.0 | 40.4 | 53.2 | | 73.1 | | 96.2 |
| G | distilled water | 13.5 | 33.5 | 51.3 | 63.8 | | 83.8 | | 91.9 |
| | J.P. first solution | 14.4 | 27.8 | 41.8 | 54.3 | | 68.9 | | 94.7 |
| H | distilled water | 4.0 | 15.3 | 26.5 | 36.4 | 45.1 | 53.8 | 60.9 | 68.9 |
| | J.P. first solution | 7.1 | 17.3 | 28.1 | 35.9 | 46.4 | 54.0 | 64.0 | 70.2 |
| I | distilled water | 12.4 | 33.1 | 48.2 | 59.5 | | 72.4 | | 82.6 |
| | J.P. first solution | 12.8 | 30.4 | 49.2 | 60.6 | | 84.3 | | 91.8 |
| J | distilled water | 11.2 | 31.1 | 47.4 | 60.5 | | 77.7 | | 90.8 |
| | J.P. first solution | 13.9 | 29.2 | 43.1 | 55.6 | 71.2 | 90.3 | | 97.2 |
| K | distilled water | 10.3 | 30.2 | 64.8 | 74.8 | | 81.9 | | |
| | J.P. first solution | 10.3 | 28.1 | 60.7 | 74.0 | | 81.6 | | |

TEST EXAMPLE 3

In Vivo Test (p.o.)

Four tablets of the slow-release sodium valproate tablets A prepared in Example 1 (total content of sodium valproate: about 800 mg) were given orally to each of 6 healthy male adults ranging in age from 22 to 29 (average age: 24.2 years) and in body weight from 56 to 78 kg (average b.w.: 64.4 kg). Changes of sodium valproate concentration in blood were observed over time. The subjects fasted for 12 hours before the test and for 4.5 hours after administration of the tablets and prohibited from taking alcohol during the testing period.

Figure 5:
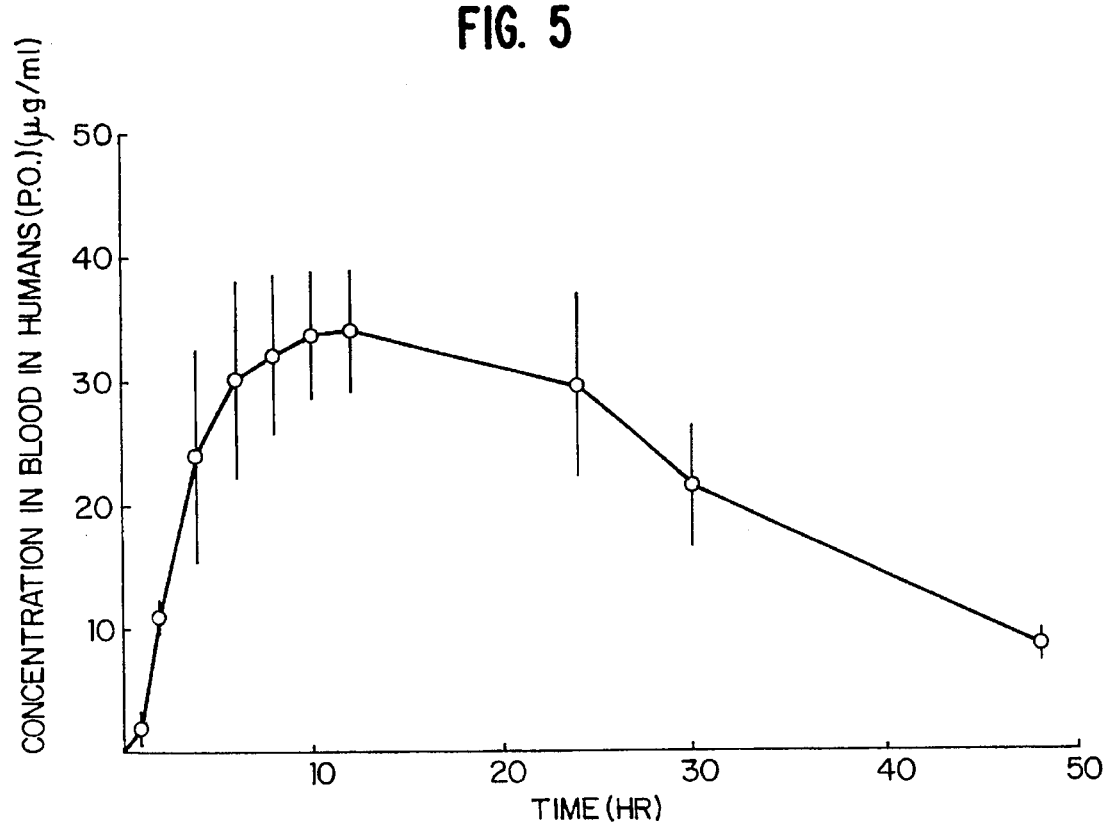
FIG. 5 is a graph of blood concentration in human (p.o.) over time of slow-release tablets of the instant invention.

Blood samples were taken immediately before administration and after 1, 2, 4, 6, 8, 10, 12, 24, 30 and 48 hours from administration. The serum was separated from the blood sample and sodium valproate content in the serum was measured by gas chromatography. The results obtained are shown in Table 3 and in FIG. 5.

TABLE 3

| Subject No. | Time After Administration (hr) | | | | | | | | | | |
|---|---|---|---|---|---|---|---|---|---|---|---|
| | 0 | 1 | 2 | 4 | 6 | 8 | 10 | 12 | 24 | 30 | 48 |
| 1 | 0.00 | 0.93 | 10.25 | 20.53 | 24.54 | 26.77 | 32.02 | 30.07 | 17.41 | 12.36 | 6.37 |
| 2 | 0.00 | 1.68 | 11.54 | 19.19 | 23.63 | 25.68 | 29.90 | 32.94 | 31.23 | 21.93 | 9.10 |
| 3 | 0.00 | 2.69 | 11.96 | 40.91 | 44.67 | 43.34 | 40.96 | 41.16 | 32.40 | 22.06 | 9.15 |
| 4 | 0.00 | 1.55 | 9.43 | 16.93 | 25.61 | 28.97 | 27.26 | 28.89 | 30.72 | 22.94 | 9.17 |
| 5 | 0.00 | 4.64 | 13.16 | 25.84 | 30.06 | 33.68 | 34.93 | 33.01 | 26.14 | 22.30 | 7.57 |
| 6 | 0.00 | 0.61 | 9.48 | 21.19 | 32.73 | 34.91 | 38.17 | 39.14 | 39.31 | 27.29 | 9.99 |
| Mean | 0.0 | 2.0 | 11.0 | 24.1 | 30.2 | 32.2 | 33.9 | 34.2 | 29.5 | 21.5 | 8.6 |
| S.D.* | 0.0 | 1.5 | 1.5 | 8.7 | 7.9 | 6.6 | 5.2 | 4.9 | 7.3 | 4.9 | 1.3 |

Note:
*S.D. stands for standard deviation.

The slow-release tablets of the instant invention maintain a stable dissolution rate in an dissolution test for a prolonged period of time without being influenced by pH conditions. Further, the tablets of the instant invention maintain a stable blood concentration of active agents, in humans (p.o.) for example, over an extended period of time and without sacrificing bioavailability.

While the invention has been described in detail and with reference to specific examples thereof, it will be apparent to one skilled in the art that various changes and modifications can be made therein without departing from the spirit and scope thereof.

What is claimed is:

1. A slow-release sodium valproate tablet comprising a core and a coating covering the surface of said core, wherein said core comprises sodium valproate and said coating comprises a mixture of ethyl cellulose and silicic acid anhydride.

2. A slow-release sodium valproate tablet as claimed claim 1, wherein said silicic acid anhydride is present in an amount of from 0.1 to 0.7 part by weight per part by weight of ethyl cellulose.

3. A slow-release sodium valproate tablet as claimed in claim 1, wherein said silicic acid anhydride is insoluble in water and dispersible in water or an organic solvent to form a colloidal dispersion.

4. A slow-release sodium valproate tablet as claimed in claim 2, wherein said silicic acid anhydride is insoluble in water and dispersible in water or an organic solvent to form a colloidal dispersion.

5. The slow-release sodium valproate tablet of claim 1 wherein said coating is in an amount of from 2 to 10% by weight based on the weight of the core.

* * * * *